United States Patent
Joshi

(10) Patent No.: US 12,029,387 B2
(45) Date of Patent: Jul. 9, 2024

(54) SURGICAL INSTRUMENT FOR PERFORMING AN ENDOSCOPY OR A LAPAROSCOPY

(71) Applicant: Mukund Raghunath Joshi, Pune (IN)

(72) Inventor: Mukund Raghunath Joshi, Pune (IN)

( * ) Notice: Subject to any disclaimer, the term of this patent is extended or adjusted under 35 U.S.C. 154(b) by 0 days.

(21) Appl. No.: 16/982,186

(22) PCT Filed: Jan. 4, 2019

(86) PCT No.: PCT/IB2019/050066
§ 371 (c)(1),
(2) Date: Sep. 18, 2020

(87) PCT Pub. No.: WO2019/180510
PCT Pub. Date: Sep. 26, 2019

(65) Prior Publication Data
US 2021/0022598 A1   Jan. 28, 2021

(30) Foreign Application Priority Data

Mar. 23, 2018 (IN) .............................. 201821010885

(51) Int. Cl.
| | |
|---|---|
| *A61B 1/00* | (2006.01) |
| *A61B 1/04* | (2006.01) |
| *A61B 1/313* | (2006.01) |
| *A61B 90/00* | (2016.01) |

(52) U.S. Cl.
CPC ...... *A61B 1/00042* (2022.02); *A61B 1/00045* (2013.01); *A61B 1/0014* (2013.01); *A61B 1/00149* (2013.01); *A61B 1/00195* (2013.01); *A61B 1/042* (2013.01); *A61B 1/3132* (2013.01); *A61B 90/37* (2016.02)

(58) Field of Classification Search
CPC .............. A61B 1/00045; A61B 1/0014; A61B 1/00195; A61B 1/042; A61B 1/3132; A61B 1/00105
See application file for complete search history.

(56) References Cited

U.S. PATENT DOCUMENTS

| | | | | |
|---|---|---|---|---|
| 5,742,429 A | * | 4/1998 | Tsumanuma | ....... A61B 1/00193 |
| | | | | 359/381 |
| 5,808,813 A | * | 9/1998 | Lucey | ...................... G02B 7/10 |
| | | | | 359/823 |
| 2010/0145146 A1 | * | 6/2010 | Melder | .............. A61B 1/00052 |
| | | | | 600/112 |
| 2011/0018988 A1 | * | 1/2011 | Kazakevich | ....... A61B 1/00105 |
| | | | | 348/E7.085 |
| 2013/0060086 A1 | | 3/2013 | Talbert et al. | |
| 2013/0176395 A1 | | 7/2013 | Kazakevich | |

\* cited by examiner

*Primary Examiner* — Aaron B Fairchild
(74) *Attorney, Agent, or Firm* — Vani Moodley, Esq.

(57) ABSTRACT

The present invention is to provide a surgical instrument for performing an endoscopy or a laparoscopy. The surgical instrument includes an adaptive element capable of holding an eyepiece of a 2D single channel endoscope and two eyepieces of a Stereo 2 channel 3D laparoscope. The adaptive element is arranged on a camera head cover of the surgical instrument. Further, the adaptive element is a holder having a cavity which allows the eyepieces of the 2D endoscope or Stereo 2 channel 3D laparoscope to fit positively therewith.

11 Claims, 7 Drawing Sheets

SURGICAL INSTRUMENT FOR PERFORMING AN ENDOSCOPY OR A LAPAROSCOPY

FIELD OF THE INVENTION

The present invention relates to a medical surgical instrument. Specifically, the present invention relates to a surgical instrument for performing an endoscopy or a laparoscopy.

BACKGROUND OF THE INVENTION

Endoscopic and laparoscopic operations are usually minimally invasive surgical procedures carried out by making a small incision on a patient's body. These instruments are provided with a visualising tool such as Endoscope and a camera for providing real-time visuals of the internal organs of the patient. The distal end is inserted through the incision on the body and the live video images are captured and displayed on a monitor. Operating surgeon does the surgery looking at the monitor. 2D Endoscopes are used for Laparoscopy, Hysteroscopy, Cystoscopy, Sinuscopy, Arthroscopy etc. and 3 D Endoscopes are predominantly used for Laparoscopy.

Currently there is no single system that can adapt both 2D endoscopes of various sizes like Laparoscope, Hysteroscopy and Cystoscope etc and 3D Laparoscope in the same camera head. Two independent systems for 2D and 3D are available which makes hospital to buy both, thereby increasing investment of hospitals.

Therefore, there is a need to provide a surgical instrument for performing both 2D endoscopy and 3D laparoscopy, which overcomes few or all of the drawbacks of the existing surgical procedures.

OBJECTS OF THE INVENTION

An object of the present invention is to provide a surgical instrument for performing an endoscopy or a laparoscopy.

Another object of the present invention is to provide a surgical instrument for performing an endoscopy or a laparoscopy, in which the eyepieces of both 2D endoscopy and 3D laparoscope can be fitted in the same camera head cover of the surgical instrument.

Yet another object of the present invention is to provide a surgical instrument for performing an endoscopy or a laparoscopy, which is economical and also improve the surgical precision with less investment.

One more object of the present invention is to provide a surgical instrument for performing an endoscopy or a laparoscopy, which reduces the time for change over during surgeries from 3D to 2D and vice versa.

Still one more object of the present invention is to provide a surgical instrument for performing an endoscopy or a laparoscopy, which reduces the space occupied in the operation theatre.

Further one more object of the present invention is to provide a surgical instrument for performing an endoscopy or a laparoscopy, which is robust in construction.

SUMMARY OF THE INVENTION

According to the present invention, there is provided a surgical instrument for performing an endoscopy or a laparoscopy. The surgical instrument includes an adaptive element capable of holding an eyepiece of a 2D single channel endoscope and two eyepieces of a Stereo 2 channel 3D laparoscope. The adaptive element is for holding the only eyepiece of the 2D single channel endoscope and two eyepieces of the Stereo 2 channel 3D laparoscope, specifically, the adaptive element is adapted to connect one of the eyepieces of a 2D single channel endoscope with various diameters and two eyepieces of the Stereo 2 channel 3D dual channel laparoscope.

The adaptive element is provided with a cavity or a cavity which allows each of the eyepieces of the 2D endoscope or Stereo 2 channel 3D laparoscope fits positively there within. Further, the adaptive element includes a locking arrangement and a focusing ring to focus the optical channel of the 2D endoscope and both the channels of the Stereo 2 channel 3D laparoscope. The locking arrangement is provided for securely locking one of the eyepieces of the 2D endoscope and both the eyepieces of the Stereo 2 channel 3D laparoscope inside the cavity. The locking arrangement may be a plunger which is operably configured manually to secure the eyepieces within the cavity.

In a locking position, when each of the eyepieces are locked inside the cavity, the locking head extends outwards. In the locked position, locking elements engage with each of the eyepieces of the 2D endoscope or both the eyepieces of the Stereo 2 channel 3D laparoscope allowing the eyepieces to lock within the cavity. In an unlocked position, the eyepieces are disengaged from locking elements thereby unlocking from the cavity. Further, the focusing ring is adjacently arranged below the cavity. The focusing ring is rotatable and configured to adjust the focal length required for the respective eyepieces. The same focusing ring can be used for both the standard 2D endoscope and 3D laparoscope.

Further, the surgical instrument is provided with a camera head cover for visualising the internal organs. In the present embodiment, the camera head cover is connected to the adaptive element. The camera head cover is also designed in such a way that it can be used for both 2D endoscopes and 3D laparoscope. The camera head cover is provided with a touch pad switch to toggle between the 2D endoscope and 3D laparoscope. Further in the present embodiment, the camera head cover is integral to the adaptive element. The adaptive element is detachable from the camera head cover but not easily detachable due to the presence of the locking arrangement. The camera head cover is provided with settings to ensure switching of 2D visual mode to 3D visual mode.

Further, a camera control unit is connected to the camera head cover using a head cable. The camera control unit can be able to convert the visuals into required projections on a monitor. The camera control unit is connectively arranged with the surgical instrument allowing monitoring and visualising required 2D visuals and 3D visuals corresponding to the medical requirement. Specifically, the camera control unit enables to replicate the 2D visuals and 3D visuals according to the respective eyepieces hold within the adaptive element. The touchpad switch facilitates in changing the mode of surgeries from the 2D endoscope to 3D laparoscope and vice versa.

BRIEF DESCRIPTION OF THE DRAWINGS

The advantages and features of the present invention will be understood better with reference to the following detailed description and claims taken in conjunction with the accompanying drawings, wherein like elements are identified with like symbols, and in which:

DETAILED DESCRIPTION OF THE INVENTION

An embodiment of this invention, illustrating its features, will now be described in detail. The words "comprising, "having, "containing," and "including," and other forms thereof, are intended to be equivalent in meaning and be open ended in that an item or items following any one of these words is not meant to be an exhaustive listing of such item or items, or meant to be limited to only the listed item or items.

The terms "first," "second," and the like, herein do not denote any order, quantity, or importance, but rather are used to distinguish one element from another, and the terms "an" and "a" herein do not denote a limitation of quantity, but rather denote the presence of at least one of the referenced items.

The present invention is to provide a surgical instrument for performing an endoscopy or a laparoscopy. Eyepieces of standard 2D Endoscope and present invention 3D Laparoscope can be fitted in the surgical instrument. The surgical instrument is economical, and it reduces the time for change over during surgery. Also reduces the space occupied in the operation theatre.

The disclosed embodiments are merely exemplary of the invention, which may be embodied in various forms.

Figure 1:
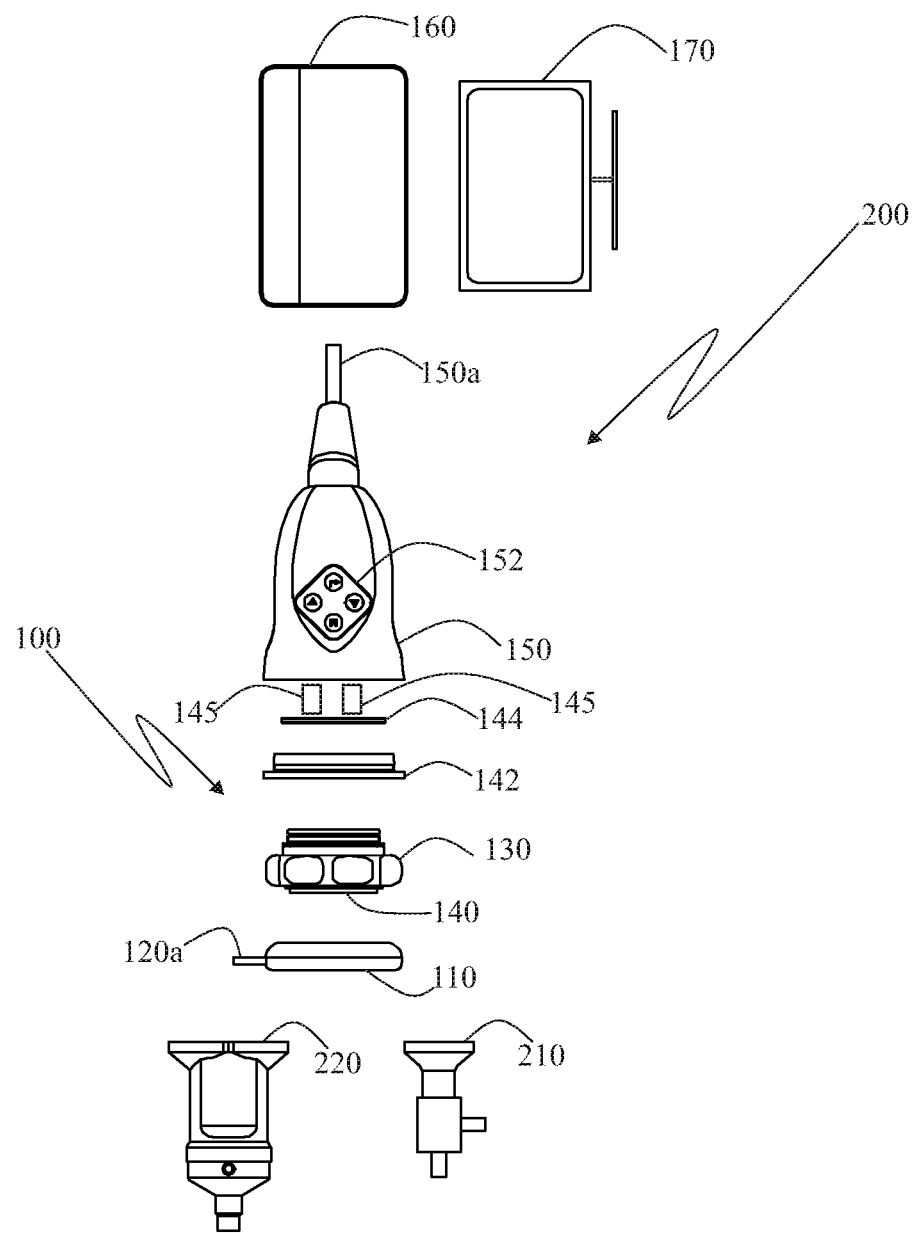
FIG. 1 illustrates a surgical instrument for performing an endoscopy or a laparoscopy.

Referring to FIG. 1, a surgical instrument 200 for performing an endoscopy or a laparoscopy in accordance with the present invention is illustrated. Specifically, the surgical instrument 200 provides an arrangement in which an endoscope or a laparoscope can be adapted to fit for performing surgeries. The surgical instrument 200 allows performing surgeries with endoscopes and laparoscopes according to the requirement of a user.

Figure 2:
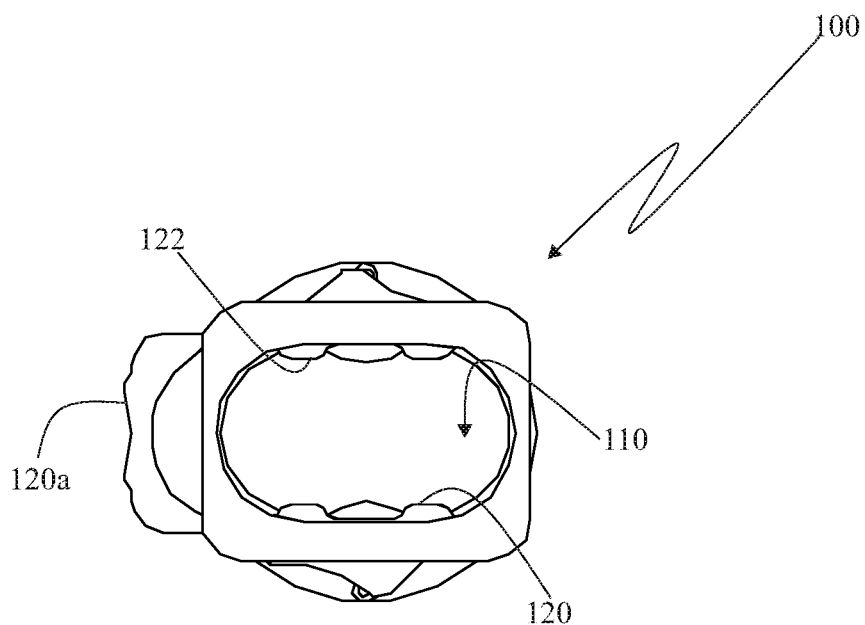
FIG. 2 illustrates a top view of an adaptive element in a locking position.

The surgical instrument 200 includes an adaptive element 100 capable of holding one of an eyepiece of a 2D single channel endoscope 210 and or two eyepieces of a Stereo 2 channel laparoscope 220. The adaptive element 100 is for holding the only eyepieces of the 2D single channel endoscope 210 and two eyepieces of the Stereo 2 channel 3D laparoscope 220, specifically, the adaptive element 100 is adapted to connect one of the eyepieces of a 2D single channel endoscope 210 with various diameters and two eyepieces of the Stereo 2 channel 3D dual channel laparoscope 220. For example, standard 2D endoscopes 210 of various diameters such as 10 mm, 5 mm, 4 mm, 2.9 mm and the like. The eyepiece of the Stereo 2 channel 3D laparoscope 220 is explicitly designed to adapt with the adaptive element 100 as shown in FIG. 2. The adaptive element 100 is capable of adapting the interchangeable eyepieces for conducting the respective surgeries. The adaptive element 100 is provided with a cavity 110 which allows each of the eyepieces of the 2D endoscope 210 or Stereo 2 channel 3D laparoscope 220 fit positively therewithin. The 2D endoscope can be a laparoscope, or a hysteroscope or a cystoscope.

Figure 3:
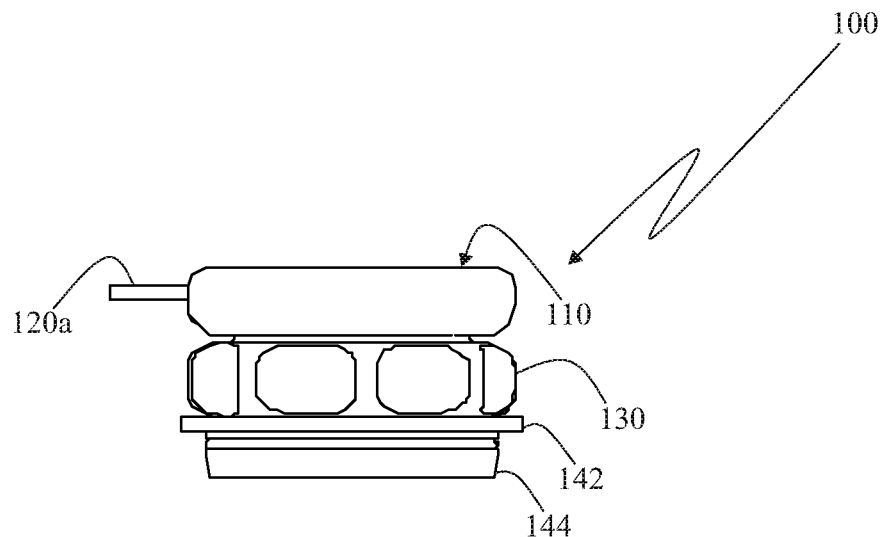
FIG. 3 illustrates a side view of the adaptive element in an unlocking position.

Further referring to FIGS. 2 and 3 the adaptive element 100 includes a locking arrangement 120 and a focusing ring 130 to focus the optical channel of the 2D endoscope 210 and both the channels of the Stereo 2 channel 3D laparoscope 220. The locking arrangement 120 is provided for securely locking one of the eyepieces of the 2D endoscope 210 and both the eyepieces of the Stereo 2 channel 3D laparoscope 220 inside the cavity 110. The locking arrangement 120 may be a plunger which is operably configured manually to secure the eyepieces within the cavity 110. The locking arrangement 120 is provided with a locking head 120a which extends outside the adaptive element 100 when each of the eyepieces are engaged within the cavity 110. The locking head 120a is slidably arranged through a slit 100a arranged on a portion of the adaptive element 100. The locking head 120a is in the vicinity of a user when the locking head 120a slides outwards through the slit 100a, allowing the user to operate the locking arrangement 120 manually.

Figure 4:
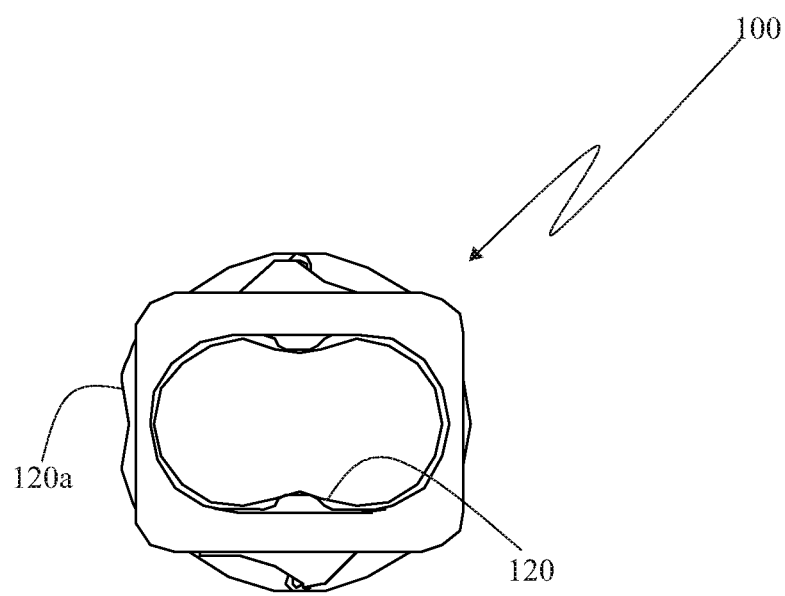
FIG. 4 illustrates a top view of the adaptive element in a locking position.
Figure 5:
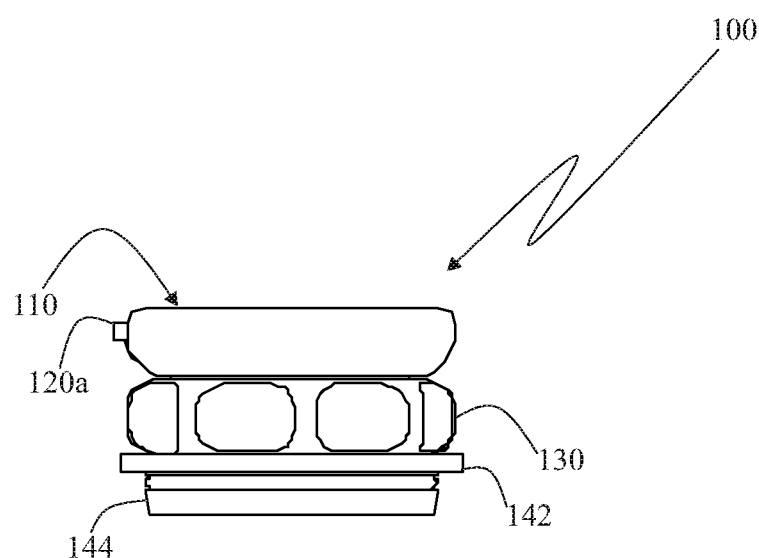
FIG. 5 illustrates a side view of the adaptive element in a locking position.
Figure 6:
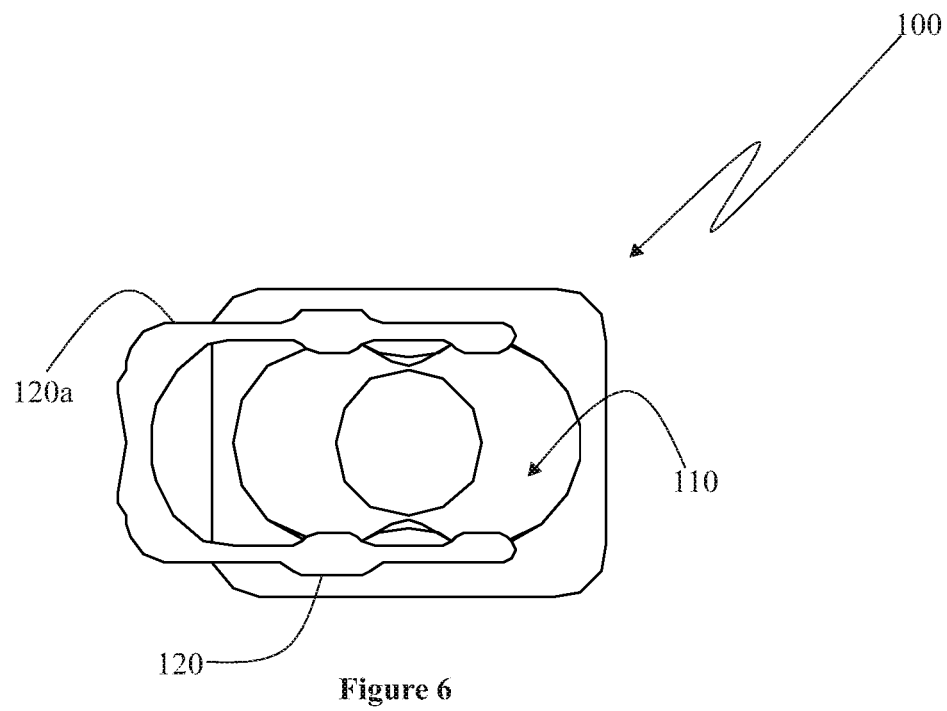
FIG. 6 illustrates another top view of an adaptive element in the locking position.
Figure 7:
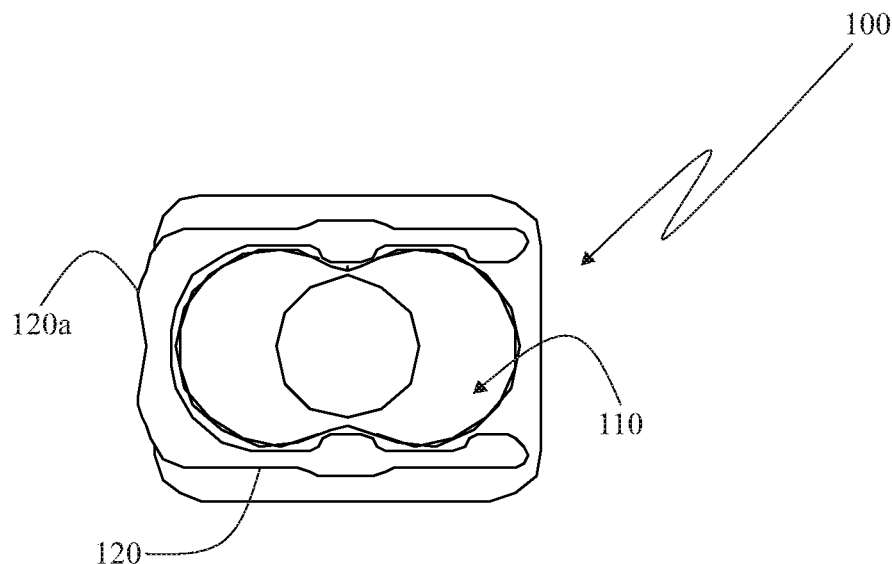
FIG. 7 illustrates another top view of an adaptive element in the unlocking position.

In a locking position as shown in FIGS. 2, 3 and 6, when each of the eyepieces are locked inside the cavity 110, the locking head 120a extends outwards. In the locked position, locking elements 122 as shown in FIG. 2 engages with each of the eyepieces of the 2D endoscope 210 or both the eyepieces of the Stereo 2 channel 3D laparoscope 220 allowing the eyepieces to lock within the cavity 110. In an unlocked position as shown in FIGS. 4, 5 and 7, the eyepieces are disengaged from the locking elements 122 thereby unlocking from the cavity 110. Specifically, upon pulling the locking head 120a of the locking arrangement 120, the locking elements 122 disengages from the eyepieces and unlock the eyepieces from the cavity 110 allowing the user to change the eyepieces.

Further, the focusing ring 130 is adjacently arranged below the cavity 110. The focusing ring 130 is rotatably configured to adjust the focal length required for the eyepieces. The focusing ring 130 can be used for both standard 2D endoscope 210 and Stereo 2 channel 3D laparoscope 220. The eyepieces are arranged on a housing 140, specifically on a top portion of the housing 140. The housing 140 is designed to seat the eyepieces therewith. A bracket 142 and a locking plate 144 is arranged to mount the adaptive element 100 as shown in FIG. 1.

Further at least two camera chip blocks 145 as shown in the FIG. 1 are clamped on the adaptive element 100. These camera chip blocks 145 are meant for capturing the image coming from the 2D endoscope or Stereo 2 channel 3D laparoscope and convert them into digital for further processing in a camera control unit 160. Distance between the two chip blocks 145 are maintained same as distance between two optical channels of stereo 2 channel 3D endoscope 220.

Figure 10:
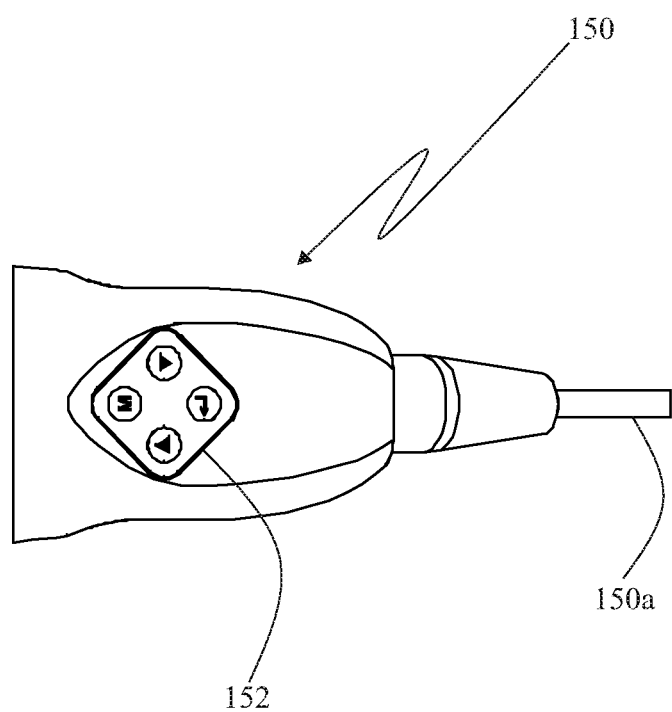
FIG. 10 illustrates an assembled view of the surgical instrument with a camera head cover having a touch pad switch to toggle between 2D endoscope and stereo 2 channel 3D laparoscope.

Further referring to FIGS. 1 and 10, the surgical instrument 200 is provided with a camera head cover 150 which is fastened with the adaptive element 100. In the present embodiment, the adaptive element 100 is arranged on the camera head cover 150. The camera head cover 150 is also designed in such a way that it can be used for both 2D endoscopes 210 and stereo 2 channel 3D laparoscope 220. The camera head cover 150 is provided with a touch pad switch 152 to toggle between 2D endoscope 210 and stereo 2 channel 3D laparoscope 220. When a 2D endoscope is connected, which has only one optical channel, only one chip block 145 gets activated through the touch pad switch 152 on the camera head cover 150 and the image on a monitor 170 shows 2D endoscope image.

Further in the present embodiment, the camera head cover 150 is integral to the adaptive element 100. The adaptive element 100 is detachable from the camera head cover 150 but not easily detachable due to the presence of the locking arrangement 120. The camera head cover 150 is provided with settings to ensure switching of 2D visual mode to 3D visual mode. Specifically, the touchpad switch 152 facilitates in changing the mode of surgeries from 2D endoscope 210 to stereo 2 channel 3D laparoscope 220 and vice versa depending on which endoscope is connected to the adaptive element 100. For example, when the touchpad switch 152 is engaged to select 2D endoscope 210 surgeries, the camera control unit 160 automatically switches off one camera sensor thereby allowing the user to visualise 2D images required for performing surgery. Similarly, upon selecting stereo 2 channel 3D laparoscope 220 via the touchpad switch (152), the camera control unit 160 automatically switches to 3D laparoscopy mode to perform the respective surgeries.

By way of non-limiting example, the touch pad switch 152 may have the following surgery modes which is visible on a camera control unit 160 TFT display.

3D Laparoscopy 10 mm
3D Laparoscopy 5 mm
2D Laparoscopy 10 mm
2D Laparoscopy 5 mm
2D Hysteroscopy 4 mm
2D Hysteroscopy 2.9 mm When the mode is switched from 3D to 2D from the camera head cover 150, suitable electronics inside the camera control unit 160 gets activated and corresponding signals are sent to the monitor 170 which is common for both 3D projections and 2D projections.

Figure 8:
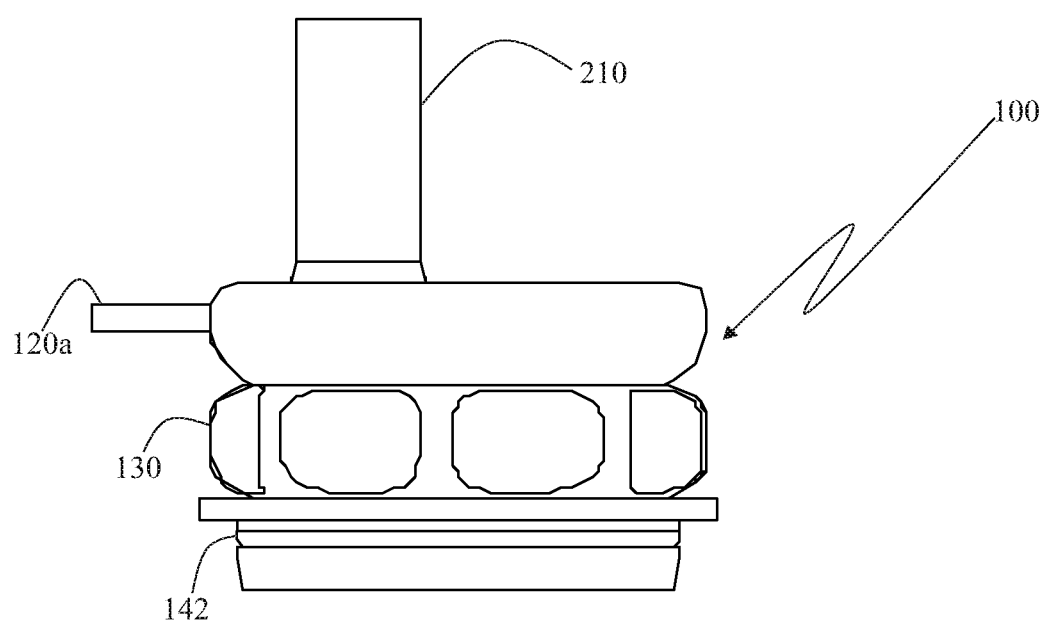
FIG. 8 illustrates an assembled view of a 2D endoscope and the adaptive element.
Figure 9:
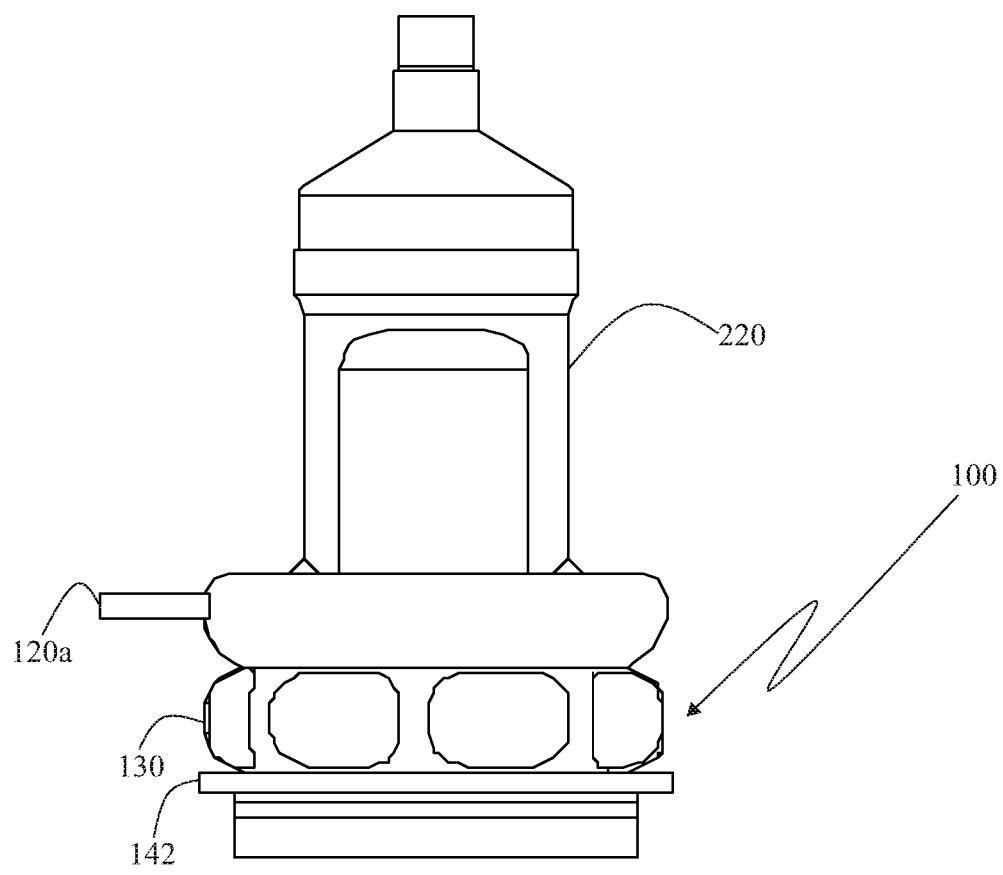
FIG. 9 illustrates an assembled view of a 3D laparoscope and the adaptive element in accordance with the present invention.

Further, the camera control unit 160 is connected to the camera head cover 150 using a head cable 150a. The camera control unit 160 can be able to convert the visuals into required projections. The camera control unit 160 is connectively arranged with the surgical instrument 200 allowing monitoring and visualising required 2D visuals and 3D visuals corresponding to the medical requirement. Specifically, the camera control unit 160 enables to replicate the 2D visuals and 3D visuals according to the respective eyepieces hold within the adaptive element 100. For example, if the eyepiece of a 2D endoscope 210 is kept in the adaptive element 100 as shown in FIG. 8, the visuals have to be represented as 2D in a monitor 170. Similarly, when a stereo 2 channel 3D laparoscope 220 eyepieces are kept in the adaptive element 100 as shown in FIG. 9, the monitor 170 has to replicate the 3D visuals with the help of the camera control unit 160. The camera control unit 160 is further connected to the camera monitor 170 to showcase the corresponding visuals captured on the camera monitor 170.

Therefore, the present invention has an advantage of providing a surgical instrument 200 for performing an endoscopy or a laparoscopy. Eyepieces of standard 2D Endoscope 210 and stereo 2 channel 3D Laparoscope 220 can be fitted in the surgical instrument 200. The surgical instrument 200 is economical, and it reduces the time for change over during surgery. Also, it reduces the space occupied in the operation theatre.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilise the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the scope of the claims of the present invention.

I claim:

1. A surgical instrument (200) for performing an endoscopy or a laparoscopy, the surgical instrument (200) comprising:
an adaptive element (100) capable of holding, one at a time, an eyepiece of a 2D single channel eyepiece endoscope (210) and two eyepieces of a Stereo 2 channel 3D laparoscope (220);
wherein the adaptive element (100) is a holder having a cavity (110) capable to fit the eyepieces of the 2D single channel eyepiece endoscope (210) or the Stereo 2 channel 3D laparoscope (220), the adaptive element (100) includes a locking arrangement (120) and a focusing ring (130) to focus optical channel of the 2D endoscope (210) and both of two optical channels of the Stereo 2 channel 3D laparoscope (220).

2. The surgical instrument 200 of claim 1, wherein the adaptive element 100 with camera chip blocks is arranged on a camera head cover 150 of the surgical instrument 200.

3. The surgical instrument 200 of claim 2, wherein the camera head cover 150 is provided with a touchpad switch 152 to toggle between the modes of surgeries from 2D endoscope and 3D laparoscope.

4. The surgical instrument 200 of claim 3, wherein when the touchpad switch 152 is engaged to select 2D endoscope 210 surgeries, the camera control unit 160 automatically switches to 2D endoscope mode thereby allowing the user to visualize 2D images required for performing surgery.

5. The surgical instrument 200 of claim 3, wherein upon selecting 3D laparoscope 220, the camera control unit 160 automatically switches to 3D laparoscopy mode to perform the respective surgeries.

6. The surgical instrument (200) of claim 1, wherein the locking arrangement (120) is for securely locking one of the eyepieces of the 2D endoscope (210) or the eyepieces of the Stereo 2 channel 3D laparoscope (220) inside the cavity 110.

7. The surgical instrument (200) of claim 1, wherein the locking arrangement (120) is provided with a locking head (120a) which extends outside the adaptive element (100) when the eyepieces of the 2D endoscope (210) or both the eyepieces of the Stereo 2 channel 3D laparoscope (220) are engaged within the cavity (110).

8. The surgical instrument 200 of claim 1, wherein a camera control unit 160 is connectively arranged with the surgical instrument 200 allowing monitoring and visualizing required 2D visuals and 3D visuals corresponding to the medical requirement.

9. The surgical instrument (200) of claim 1, wherein the adaptive element 100 is mounted on a camera head cover (150) of the surgical instrument and the adaptive element (100) has two camera chip (145) blocks clamped thereon, the camera chip blocks are for capturing the image coming from the 2D endoscope or Stereo 2 channel 3D laparoscope and converting them into digital for further processing in a camera control unit (160) wherein when 2D endoscope is selected via a touch pad switch on the camera head, one of the chip block stops working and then 2D image is shown to a surgeon on a monitor.

10. The surgical instrument (200) of claim 9, wherein the touchpad switch (152) is to toggle between the modes of surgeries from 2D endoscope and 3D laparoscope.

11. The surgical instrument (200) of claim 1 wherein the 2D endoscope can be a laparoscope, or a hysteroscope or a cystoscope.

\* \* \* \* \*